(12) United States Patent
Qiao et al.

(10) Patent No.: US 9,314,519 B2
(45) Date of Patent: *Apr. 19, 2016

(54) LIQUID STABLE VIRUS VACCINES

(71) Applicant: Intervet Inc., Summit, NJ (US)

(72) Inventors: Zhisong Qiao, Omaha, NE (US); Kevin O'Connell, Omaha, NE (US)

(73) Assignee: Intervet Inc., Madison, NJ (US)

( * ) Notice: Subject to any disclaimer, the term of this patent is extended or adjusted under 35 U.S.C. 154(b) by 66 days.

This patent is subject to a terminal disclaimer.

(21) Appl. No.: 13/967,847

(22) Filed: Aug. 15, 2013

(65) Prior Publication Data

US 2014/0056942 A1 Feb. 27, 2014

Related U.S. Application Data

(60) Provisional application No. 61/777,164, filed on Mar. 12, 2013, provisional application No. 61/691,507, filed on Aug. 21, 2012.

(51) Int. Cl.

| A61K 47/42 | (2006.01) |
|---|---|
| A61K 39/155 | (2006.01) |
| A61K 39/175 | (2006.01) |
| A61K 47/10 | (2006.01) |
| A61K 47/18 | (2006.01) |
| A61K 47/20 | (2006.01) |
| A61K 47/22 | (2006.01) |
| A61K 47/26 | (2006.01) |
| A61K 39/23 | (2006.01) |
| A61K 39/235 | (2006.01) |
| A61K 39/145 | (2006.01) |
| A61K 39/12 | (2006.01) |
| A61K 9/08 | (2006.01) |
| A61K 39/02 | (2006.01) |
| C12N 7/00 | (2006.01) |
| A61K 39/00 | (2006.01) |

(52) U.S. Cl.

CPC ............. *A61K 39/235* (2013.01); *A61K 9/08* (2013.01); *A61K 39/0225* (2013.01); *A61K 39/12* (2013.01); *A61K 39/145* (2013.01); *A61K 39/155* (2013.01); *A61K 39/175* (2013.01); *A61K 39/23* (2013.01); *A61K 47/10* (2013.01); *A61K 47/183* (2013.01); *A61K 47/20* (2013.01); *A61K 47/22* (2013.01); *A61K 47/26* (2013.01); *A61K 47/42* (2013.01); *C12N 7/00* (2013.01); *A61K 2039/521* (2013.01); *A61K 2039/5252* (2013.01); *A61K 2039/5254* (2013.01); *A61K 2039/552* (2013.01); *A61K 2039/70* (2013.01); *C12N 2710/10034* (2013.01); *C12N 2750/14034* (2013.01); *C12N 2750/14322* (2013.01); *C12N 2760/18034* (2013.01); *C12N 2760/18434* (2013.01); *C12N 2760/18634* (2013.01)

(58) Field of Classification Search
None
See application file for complete search history.

(56) References Cited

U.S. PATENT DOCUMENTS

| 3,155,589 A * | 11/1964 | Slater ...................... 424/202.1 |
|---|---|---|
| 4,337,242 A | 6/1982 | Markus et al. |
| 4,451,569 A | 5/1984 | Kobayashi et al. |
| 5,443,959 A | 8/1995 | Kikuchi et al. |
| 5,565,318 A | 10/1996 | Walker et al. |
| 5,593,824 A | 1/1997 | Treml et al. |
| 5,763,409 A | 6/1998 | Bayol et al. |
| 5,932,223 A | 8/1999 | Burke et al. |
| 6,039,958 A | 3/2000 | Koyama et al. |
| 6,231,860 B1 | 5/2001 | Fanget et al. |
| 6,331,303 B1 | 12/2001 | Briggs et al. |
| 6,931,888 B2 | 8/2005 | Shekunov et al. |
| 7,073,349 B2 | 7/2006 | Shekunov et al. |
| 7,351,416 B2 | 4/2008 | Briggs et al. |
| 7,959,929 B2 | 6/2011 | Crawford et al. |
| 8,192,747 B2 | 6/2012 | Vande Velde |
| 8,980,610 B2 | 3/2015 | Selvitelli et al. |
| 2004/0038878 A1 | 2/2004 | Tanikawa et al. |
| 2004/0154317 A1 | 8/2004 | Shekunov et al. |
| 2005/0178020 A1 | 8/2005 | Shekunov et al. |
| 2007/0148765 A1* | 6/2007 | Evans et al. ............... 435/320.1 |
| 2007/0161085 A1* | 7/2007 | Trager et al. ............... 435/69.1 |
| 2007/0190163 A1 | 8/2007 | Malaknov et al. |
| 2007/0259348 A1 | 11/2007 | Phadke et al. |
| 2008/0248551 A1* | 10/2008 | Stinchcomb et al. .......... 435/236 |
| 2009/0010955 A1* | 1/2009 | Kapil et al. ............... 424/186.1 |
| 2009/0274734 A1 | 11/2009 | Daamen et al. |
| 2010/0015180 A1 | 1/2010 | Francon et al. |
| 2010/0124557 A1 | 5/2010 | Oberreither et al. |
| 2010/0196420 A1 | 8/2010 | Kapil et al. |
| 2010/0297231 A1 | 11/2010 | Vehring et al. |
| 2011/0081380 A1 | 4/2011 | Francon et al. |
| 2012/0213810 A1 | 8/2012 | Burgard et al. |
| 2014/0056942 A1 | 2/2014 | Qiao et al. |

FOREIGN PATENT DOCUMENTS

| EP | 0028563 A1 | 5/1981 |
|---|---|---|
| EP | 0650734 | * 10/1993 |

(Continued)

OTHER PUBLICATIONS

Derwent English abstract of JP 61053227 Sasaki et al. Mar. 1986.*

(Continued)

*Primary Examiner* — Shanon A Foley

(57) ABSTRACT

The present invention discloses liquid stable vaccines that comprise a live attenuated virus, 10-30% sugar additive, and an amino acid. The present invention also discloses the manufacture of such vaccines and methods of protecting an animal by administration of such vaccines.

21 Claims, No Drawings

(56) References Cited

FOREIGN PATENT DOCUMENTS

| | | | |
|---|---|---|---|
| EP | 1123710 A1 | | 8/2001 |
| GB | 1575155 | | 9/1980 |
| JP | 61053227 | * | 3/1986 |
| WO | WO8906973 A1 | | 8/1989 |
| WO | WO03087327 A2 | | 10/2003 |
| WO | WO2004017990 A1 | | 3/2004 |
| WO | WO 2007035455 | * | 3/2007 |
| WO | 2010125084 A1 | | 11/2010 |
| WO | 2010125087 A1 | | 11/2010 |
| WO | 2011072218 | | 6/2011 |
| WO | WO2009092703 A1 | | 6/2011 |
| WO | WO2014009328 A1 | | 1/2014 |
| WO | WO2014029702 A1 | | 2/2014 |
| WO | WO2014140239 A1 | | 9/2014 |
| WO | WO2015044337 A2 | | 4/2015 |
| WO | WO2015121463 A2 | | 8/2015 |
| WO | WO2015124594 A1 | | 8/2015 |

OTHER PUBLICATIONS

Burke, et al., "Formulation Stability, and Delivery of Live Attenuated Vaccines for Human Use", Critical Reviews in Therapeutic Drug Carrier Systems, 1999, pp. 1-83, vol. 16(1).

The UK's Favourite Small Animal Vaccines; The Novivac Range, 2006, XP002714516, retrieved from the Internet: URL:http://customers.msd-animal-health.co.uk/binaries/Nobivac_Range_of_Small_Animal_Vaccines_047302_tcm79-69698.pdf (retrieved on Oct. 10, 2013).

Nobivac DHPPi; Combined Live Attenuated Freeze-Dried Canine Distemper Virus, Adenovirus Type 2, Parvovirus and Parainfluenza Virus Vaccine, XP-002714517, retrieved from the Internet:URL:http://www.msd-animal-health.co.nz/binaries/Nobivac_DHPPi_website_label_Feb_12_tcm51-37104.pdf (retrieved on Oct. 10, 2013).

PCT International Search Report for corresponding PCT/EP2013/067169, mailed on Oct. 25, 2013, 4 pages.

Crawford et al., "Transmission of Equine Influenza Virus to Dogs", Science, 2005, pp. 482-485, vol. 310.

Taguchi et al., "Antibody titers for canine parvovirus type-2, canine distemper virus, and canine adenovirus type-1 in adult household dogs", Canine Veterinary Journal, 2011, pp. 983-986, vol. 52.

Ausar, et al., "High-throughput Screening of Stabilizers for Respiratory Syncytial Virus, Identification of Stabilizers and their Effects on the Conformational Thermostabilility of Viral Particles", Human Vaccines, 2007, pp. 68-77, vol. 3 (3).

Ausar, et al., "Analysis of the thermal and pH stability of human respiratory syncytial virus", Molecular Pharmaceutics, 2005, pp. 491-499, vol. 2(6).

Chokephaibulkit, et al., "Challenges for the formulation of a universal vaccine against dengue", Experimental Biology and Medicine, 2013, pp. 566-578, vol. 238.

Medi, et al.., "Excipient selection in biologics and vaccines formulation development", European Pharmaceutical Review, 2014, pp. 16-20, 19(1).

Mochizuki, Masami, "Growth characteristics of canine pathogenic viruses in MDCK cells cultured in RPMI 1640-medium without animal protein", Vaccine, 2006, pp. 1744-1748, vol. 24.

Garry L. Morefield, "A Rational, Systematic Approach for the Development of Vaccine Formulations", The AAPS Journal, 2011, pp. 191-200, vol. 13(2).

Arakawa, et al., Biotechnology applications of amino acids in protein purification and formulations, Amino Acids, 2007, 587-605, 33.

Brandau, et al., Thermal Stability of Vaccines, Journal of Pharmaceutical Sciences, 2003, 218-231, 92-2.

Cavanagh, et al., Coronavirus avian infectious bronchitis virus, Veterinary Research, 2007, pp. 281-297.

Chen, et al., Opportunities and challenges of developing thermostable vaccines, Expert Reviews, 2009, 547-557, 8-5.

Ellingson, et al., Vaccine efficacy of porcine reproductive and respiratory Syndrome Virus Chimeras, Vaccine, 2010, pp. 2679-2686, 28.

Kamerzell, et al., Protein-excipient interactions: Mechanisms and biophysical characterization applied to protein formulation development, Advanced Drug Delivery Reviews, 2011, 1118-1159, 63.

Patel, et al., Stability Consideration for Biopharmaceuticals, Part 1, BioProcess Technical, 2011, 1-10.

Saif, Linda, Bovine Respiratory Coronavirus, Veterinary Clinics of North America: Food Animal Practice, 2010, pp. 349-364, 26(2), US.

Schlehuber, et al., Towards Ambient Temperature-stable vaccines: The identification of thermally stabilizing liquid formulations for measles virus using an innovative high-throughput infectivity assay, Vaccine, 2011, pp. 5031-5039, 29.

Papatsiros, Porcine Respiratory and Reproduction Syndrome Virus Vaccinology: A Review for Commercial Vaccines, American Journal of Animal and Veterinary Sciens, 2012, pp. 149-158, 7-4.

* cited by examiner

LIQUID STABLE VIRUS VACCINES

CROSS-REFERENCE TO RELATED APPLICATIONS

This application claims priority under 35 U.S.C. §119(e) of provisional application U.S. Ser. Nos. 61/691,507 filed Aug. 21, 2012; and 61/777,164 filed Mar. 12, 2013, the contents of which are hereby incorporated by reference in their entireties.

FIELD OF THE INVENTION

The present invention pertains to liquid stable vaccines that comprise a live attenuated virus. The invention also pertains to the manufacture of such vaccines and methods of vaccinating animal subjects.

BACKGROUND

There are a significant number of viruses that can infect dogs and/or cats. While symptoms due to the corresponding virus infections for example, can include mild cold-like symptoms, others can be rapidly fatal, as in the case of canine distemper virus (CDV) infections [see e.g., US2010/0196420]. Indeed, CDV triggers a multi-systemic infection that may involve the ocular, respiratory, gastrointestinal, integument, and nervous systems. The mortality rate from canine parvovirus (CPV) is also relatively high [see e.g., US2009/0010955]. CPV is primarily an enteric pathogen that infects dogs, especially young dogs, and is characterized by acute diarrhea, fever, and leukopenia in dogs and puppies more than 4 to 5 weeks old. Even younger puppies can suffer myocardial disease. Canine distemper virus and canine parvovirus are the two most important canine viruses to protect puppies/dogs from.

Additional canine viruses include: canine parainfluenza (CPI) virus, which is a highly contagious virus that causes respiratory illnesses contributing to the contraction of upper respiratory diseases and infectious tracheobronchitis; canine adenovirus type-1 (CAV1) which leads to infectious hepatitis; and canine influenza virus (CIV) which is highly contagious and can cause a severe type of respiratory disease. CIV has been reported to be capable of causing 100% infection with 80% morbidity, and up to 5-8% mortality in severe infections [Crawford et al., *Science* 310(5747):482-485 (2005); U.S. Pat. No. 7,959,929 B2]. Similarly, there are a number of feline viruses that afflict cats including feline calicivirus (FCV), feline leukemia virus (FeLV), feline panleukopenia virus (FPLV), feline coronavirus (FCoV), and feline rhinotracheitis (FVR) virus.

It is now widely accepted that the best way of preventing disease due to canine or feline virus infections is to vaccinate them against these viruses. Indeed, canine distemper virus vaccines have significantly reduced the prevalence of the corresponding disease. Similarly, infectious canine hepatitis has been extremely limited by canine adenovirus-2 vaccines (CAV2). The use of live attenuated CAV2 in vaccines in place of closely related CAV1 eliminates concerns regarding the interstitial nephritis and corneal opacity observed in dogs that have been inoculated with live attenuated CAV1 [Taguchi et al., *Can Vet J.* 52(9): 983-986 (2011)].

Moreover, multivalent live attenuated virus vaccines can be safely administered that limit the number of vaccine injections required. Accordingly, there are several commercially available multivalent live attenuated virus vaccines that protect against canine distemper, canine infectious hepatitis, canine parvovirus, and canine parainfluenza virus. In addition, newer multivalent vaccines further protect against canine influenza virus as well.

Heretofore, attenuated canine and feline viruses have been unstable when stored in liquid solutions. Therefore, most live attenuated canine or feline virus vaccines are lyophilized, i.e., freeze-dried, prior to their long-term storage. The live attenuated canine or feline virus is commonly mixed as a suspension in water with a protective agent, frozen, and then dehydrated by sublimation and secondary drying during the lyophilization process. The low temperatures of freezing and drying by sublimation, together with the low surface to volume ratios involved, can require long drying periods and thereby, significantly increase manufacturing time and costs.

In addition, there are inherent inconsistencies in large commercial drying processes due to: the inability to adjust the shelf temperature across the entire product load, variable freezing rates across the dryer, edge effects, and radiant energy effects. Increasing the drying temperature to reduce drying times is often not an option since the drying temperature has to remain significantly below the glass-transition temperature of the protective protein matrix. Moreover, the long inconsistent drying times and/or high drying temperatures often lead to structural damage to the live attenuated viruses, along with a significant loss of their biologic activity.

Consequently, in order to account for the inherent loss in efficacy, lyophilized canine and/or feline vaccines that comprise live attenuated viruses are stored with augmented titers. However, such increased titers can lead to significant adverse events should the lyophilization process actually lead to less loss of activity than anticipated. Therefore, great care is required to formulate a vaccine to contain a virus titer that is not only safely below the amount that leads to adverse events, but that also maintains sufficient efficacy in view of the virus titer loss due to lyophilisation and subsequent storage. Therefore, there is a need for new live attenuated canine and/or feline virus vaccines that can reliably retain their virus titers at a safe and efficacious level.

The citation of any reference herein should not be construed as an admission that such reference is available as "prior art" to the instant application.

SUMMARY OF THE INVENTION

In order to overcome the deficiencies of current vaccines, the present invention provides novel liquid stable, live, attenuated virus vaccines, as well as their corresponding immunogenic compositions. In certain embodiments, the live attenuated virus is a live attenuated canine virus. In other embodiments, the live attenuated virus is a live attenuated feline virus. The present invention also provides methods of administering such vaccines to an animal. The present invention further provides methods of preventing a disease in an animal through administering a vaccine of the present invention. In particular embodiments, the animal is a canine. In other embodiments, the animal is a feline.

Accordingly, the present invention provides liquid stable vaccines that comprise a live attenuated virus. In particular embodiments, the vaccine comprises a sugar additive and an amino acid. In certain embodiments of this type, the vaccine comprises 10 to 30% sugar additive. In particular embodiments, the vaccine comprises 12 to 27% sugar additive. In certain embodiments, the vaccine comprises 15 to 25% sugar additive. In related embodiments the vaccine comprises 15 to 20% sugar additive. In other embodiments, the vaccine comprises 20 to 25% sugar additive. In more particular embodiments, the vaccine comprises 16 to 18% sugar additive. In even more particular embodiments, the vaccine comprises 17% sugar additive.

In particular embodiments of the liquid stable virus vaccines of the present invention the sugar additive is sucrose. In other embodiments the sugar additive is sorbitol. In still other embodiments, the sugar additive is mannitol. In yet other embodiments, the sugar additive is trehalose. In still other embodiments, the sugar additive is dextrose. In particular embodiments the sugar additive is actually a combination of two or more sugar additives. In a particular embodiment of this type, the sugar additive is a combination of sucrose and sorbitol. In a more particular embodiment of this type, the sugar additive is a combination of 15% sucrose and 10% sorbitol.

The liquid stable vaccines of the present invention can range in pH from pH 6.0 to pH 8.0. In certain embodiments the pH range is from pH 6.5 to pH 7.8. In particular embodiments the pH range is from pH 6.8 to pH 7.5. In more particular embodiments the pH range is from pH 7.0 to pH 7.4. In an even more particular embodiment the pH is 7.2.

The liquid stable vaccines of the present invention can comprise a buffer. In a particular embodiment of this type, the buffer comprises 2.5 to 50 mM Tris. In a related embodiment, the buffer comprises 5 to 25 mM Tris. In particular embodiments, the buffer comprises 10 to 20 mM Tris. In yet other embodiments the buffer can comprise 2.5 to 50 mM histidine. In particular embodiments the buffer comprises 2.5 to 50 mM Tris and 2.5 to 50 mM histidine. In more particular embodiments the buffer comprises 5 to 25 mM Tris and 5 to 25 mM histidine. In still more particular embodiments the buffer comprises 10 to 20 mM Tris and 10 to 20 mM histidine. In other embodiments the buffer comprises 2.5 to 50 mM phosphate. In a related embodiment, the buffer comprises 5 to 25 mM phosphate. In particular embodiments, the buffer comprises 10 to 20 mM phosphate.

The liquid stable vaccines of the present invention comprise an amino acid. In certain embodiments the amino acid is arginine. In other embodiments, the amino acid is methionine. In still other embodiments, the amino acid is glycine. In yet other embodiments, the amino acid is glutamic acid. In related embodiments, the liquid stable vaccines comprise both arginine and methionine. In other embodiments, the liquid stable vaccines comprise both arginine and glycine. In yet other embodiments, the liquid stable vaccines comprise both glycine and methionine. In related embodiments, the liquid stable vaccines comprise both glutamic acid and methionine. In other embodiments, the liquid stable vaccines comprise both glutamic acid and glycine. In yet other embodiments, the liquid stable vaccines comprise both glutamic acid and arginine. In related embodiments, the liquid stable vaccines comprise arginine, glutamic acid, and methionine. In other embodiments, the liquid stable vaccines comprise arginine, glutamic acid, and glycine. In yet other embodiments, the liquid stable vaccines comprise arginine, glutamic acid, and methionine. In still other embodiments, the liquid stable vaccines comprise arginine, glycine, and methionine. In yet other embodiments, the liquid stable vaccines comprise arginine, glycine, and methionine. In particular embodiments, the liquid stable vaccines comprise arginine, glycine, methionine, and glutamic acid.

In particular embodiments the final concentration of arginine, or glutamic acid, or glycine in the liquid stable vaccine is 0.15 to 0.6 M. In related embodiments, the final concentration of arginine, or glutamic acid, or glycine in the liquid stable vaccine is 0.2 to 0.5 M. In more particular embodiments, the final concentration of arginine, or glutamic acid, or glycine in the liquid stable vaccine is 0.25 to 0.35 M. In even more particular embodiments, the final concentration of arginine, or glutamic acid, or glycine in the liquid stable vaccine is 0.3 M.

In particular embodiments the final combined concentration of arginine, and/or glutamic acid, and/or glycine in the liquid stable vaccine is 0.15 to 0.6 M. In related embodiments, the final combined concentration of arginine, and/or glutamic acid, and/or glycine in the liquid stable vaccine is 0.2 to 0.5 M. In more particular embodiments, the final combined concentration of arginine, and/or glutamic acid, and/or glycine in the liquid stable vaccine is 0.25 to 0.35 M. In even more particular embodiments, the final combined concentration of arginine, and/or glutamic acid, and/or glycine in the liquid stable vaccine is 0.3 M.

In particular embodiments the final concentration of methionine in the liquid stable vaccine is 0.025 to 0.3 M. In related embodiments, the final concentration of methionine in the liquid stable vaccine is 0.04 to 0.15 M. In more particular embodiments, the final concentration of methionine in the liquid stable vaccine is 0.06 to 0.09 M. In even more particular embodiments, the final concentration of methionine in the liquid stable vaccine is 0.07 M.

The liquid stable vaccines of the present invention also can comprise a stabilizer protein. The stabilizer protein can be an intact protein and/or a protein hydrolysate. In particular embodiments the stabilizer protein is gelatin. In more particular embodiments the stabilizer protein contained by the liquid stable vaccine of the present invention is 0.4 to 1.6% gelatin. In alternative embodiments the stabilizer protein is a hydrolysate of whole casein. In particular embodiments of this type the stabilizer protein contained by the liquid stable vaccine of the present invention is 0.5-2.0% of a hydrolysate of whole casein. In certain embodiments the hydrolysate of whole casein is a proteolytic hydrolysate of whole casein.

In addition, the liquid stable vaccines of the present invention can also further comprise an alcohol. In particular embodiments of this type the alcohol is ethanol. In more particular embodiments the liquid stable vaccine comprises 0.25 to 1.0% ethanol. In addition, the liquid stable vaccines of the present invention can also further comprise a chelating agent. In particular embodiments the chelating agent is EDTA. In more particular embodiments the liquid stable vaccine comprises 50 to 200 µM EDTA. In certain embodiments the liquid stable vaccines of the present invention can further comprise a free radical scavenger and/or an antioxidant. In related embodiments, the liquid stable vaccines of the present invention are maintained in sealed containers that have an inert gas such as argon, nitrogen, or helium, above the liquid (e.g., have been back-filled with the inert gas).

The liquid stable vaccines of the present invention can comprise a live attenuated canine virus. In certain embodiments the live attenuated canine virus is canine distemper virus. In other embodiments the live attenuated canine virus is canine adenovirus type 2. In yet other embodiments the live attenuated canine virus is canine parvovirus (CPV). In one particular embodiment of this type, the canine parvovirus is a canine parvovirus 2b (CPV-2b). In another particular embodiment of this type, the canine parvovirus is a canine parvovirus 2c (CPV-2c). In a specific embodiment of this type, the CPV-2c is ATCC accession No. PTA-13492. In yet another embodiment the canine parvovirus is a recombinant canine parvovirus that has been constructed to comprise a heterogenous CPV-2c/CPV-2 genome, i.e., the region encoding the capsid proteins is from a CPV-2c isolate and the region encoding the nonstructural proteins is from a CPV-2 isolate.

In still other embodiments the live attenuated canine virus is canine parainfluenza virus. In yet other embodiments the live attenuated canine virus is canine coronavirus. In still other embodiments the live attenuated canine virus is canine pneumovirus. In yet other embodiments the live attenuated canine virus is infectious canine hepatitis virus. In still other embodiments the live attenuated canine virus is canine herpes virus. In yet other embodiments the live attenuated canine virus is rabies virus. In still other embodiments the live attenuated canine virus is canine minute virus. In yet other embodiments the live attenuated canine virus is canine influenza virus. In alternative embodiments the live attenuated virus is a pseudorabies virus.

The liquid stable vaccines of the present invention can comprise a live attenuated feline virus. In certain embodiments the live attenuated feline virus is feline herpesvirus (FHV). In other embodiments the live attenuated feline virus is feline calicivirus (FCV). In yet other embodiments the live attenuated feline virus is feline pneumovirus (FPN). In still other embodiments the live attenuated feline virus is feline parvovirus (FPV). In yet other embodiments the live attenuated feline virus is feline leukemia virus (FeLV). In still other embodiments the live attenuated feline virus is feline infectious peritonitis virus (FIPV). In yet other embodiments the live attenuated feline virus is feline immunodeficiency virus (FIV). In still other embodiments the live attenuated feline virus is borna disease virus (BDV). In yet other embodiments the live attenuated feline virus is feline influenza virus. In still other embodiments the live attenuated feline virus is feline panleukopenia virus (FPLV). In yet other embodiments the live attenuated feline virus is feline coronavirus (FCoV). In still other embodiments the live attenuated feline virus is feline rhinotracheitis virus (FVR).

In addition, the present invention provides liquid stable vaccines that are multivalent vaccines. In particular embodiments the multivalent vaccines of the present invention comprise only live attenuated virus vaccines. Such multivalent vaccines can contain any combination of live attenuated viruses. In particular embodiments of this type, the multivalent vaccine comprises live attenuated canine distemper virus and live attenuated canine parvovirus. In related embodiments the multivalent vaccine comprises live attenuated canine distemper virus and live attenuated canine adenovirus type 2. In other embodiments the multivalent vaccine comprises live attenuated canine distemper virus and live attenuated canine parainfluenza virus. In still other embodiments the multivalent vaccine comprises live attenuated canine distemper virus, live attenuated canine parvovirus, and live attenuated canine parainfluenza virus. In yet other embodiments the multivalent vaccine comprises live attenuated canine distemper virus, live attenuated canine parvovirus, and live attenuated canine adenovirus type 2. In still other embodiments the multivalent vaccine comprises live attenuated canine distemper virus, live attenuated canine parainfluenza virus, and live attenuated canine adenovirus type 2. In yet other embodiments the multivalent vaccine comprises live attenuated canine distemper virus, live attenuated canine parvovirus, live attenuated canine parainfluenza virus, and live attenuated canine adenovirus type 2. In particular embodiments the multivalent vaccine comprises live attenuated canine distemper virus, live attenuated canine parvovirus, live attenuated canine parainfluenza virus, live attenuated canine adenovirus type 2, and live attenuated canine coronavirus. In related embodiments the multivalent vaccine comprises live attenuated canine distemper virus, live attenuated canine parvovirus, live attenuated canine parainfluenza virus, live attenuated canine adenovirus type 2, and live attenuated feline coronavirus. In particular embodiments of this type, the multivalent vaccine comprises live attenuated canine distemper virus, live attenuated canine adenovirus type 2, live attenuated canine parvovirus, live attenuated canine parainfluenza virus, and live attenuated canine influenza virus.

In other embodiments the present invention provides liquid stable vaccines that are multivalent vaccine that comprise live attenuated canine adenovirus type 2 and live attenuated canine parainfluenza virus. In yet other embodiments the multivalent vaccine comprises live attenuated canine adenovirus type 2 and live attenuated canine parvovirus. In yet other embodiments the multivalent vaccine comprises live attenuated canine parvovirus and live attenuated canine parainfluenza virus. In still other embodiments the multivalent vaccine comprises live attenuated canine adenovirus type 2, live attenuated canine parvovirus, and live attenuated canine parainfluenza virus. In particular embodiments of this type, the multivalent vaccine comprises live attenuated canine adenovirus type 2, live attenuated canine parvovirus, live attenuated canine parainfluenza virus, and live attenuated canine influenza virus.

The present invention further provides methods of aiding in the protection of a feline or canine against a clinical disease that arises from a canine or feline virus infection comprising administering a vaccine of the present invention to the animal. In certain embodiments the administration is performed mucosally. In other embodiments the administration is performed parenterally. In still other embodiments the administration is performed intradermally. In yet other embodiments the administration is performed transdermally. In more specific embodiments, a vaccine of the present invention is administered to the animal subcutaneously. In other specific embodiments, a vaccine of the present invention is administered to the animal intramuscularly. The present invention also includes the use of primary and/or booster vaccines.

In particular embodiments, the animal subject is a canine and the method comprises administering to the canine a liquid stable vaccine of the present invention that comprises a live attenuated virus. In specific embodiments the liquid stable vaccine comprises live attenuated canine distemper virus, live attenuated canine adenovirus type 2, live attenuated canine parvovirus, and live attenuated canine parainfluenza virus. In certain embodiments of this type, the liquid stable vaccine comprises live attenuated canine distemper virus, live attenuated canine adenovirus type 2, live attenuated canine parvovirus, live attenuated canine parainfluenza virus, and live attenuated canine influenza virus.

Methods of making any and all of the liquid stable vaccines of the present invention are also provided. In certain embodiments the method comprises combining a therapeutically effective amount of a live attenuated virus with a 10-30% sugar additive, an amino acid, and a buffered solution at pH 6.0 to pH 8.0 to form a liquid stable vaccine. The amino acid can be arginine, glycine, glutamic acid, methionine, or combinations of arginine, glycine, glutamic acid and/or methionine. In particular embodiments the arginine and/or glycine and/or glutamic acid has a final concentration of 0.15 to 0.6 M in the liquid stable vaccine. In certain embodiments the methionine has a final concentration of 0.025 to 0.3 M in the liquid stable vaccine. In particular embodiments the therapeutically effective amount of a live attenuated virus is a therapeutically effective amount of a live attenuated canine virus. In specific embodiments of this type, the therapeutically effective amount of a live attenuated canine virus includes therapeutically effective amounts of live attenuated canine distemper virus, live attenuated canine adenovirus type 2, live attenuated canine parvovirus, and live attenuated canine parainfluenza virus.

These and other aspects of the present invention will be better appreciated by reference to the following Detailed Description.

DETAILED DESCRIPTION OF THE INVENTION

In contrast to killed virus vaccines, the liquid stable live virus vaccines of the present invention are attenuated. Heretofore, particular care would need to be taken when formulating such an attenuated live virus vaccine to maintain the titer of the attenuated viruses at a level that is safely below that which can lead to a significant adverse event. Indeed, most live attenuated canine or feline virus vaccines are lyophilized, and lyophilization can lead to substantial declines in the efficacy of the attenuated live virus vaccines both due to the lyophilization process itself, as well as over time during long-term storage.

The present invention has overcome this problem by providing liquid stable vaccines that remain efficacious, even during storage, without needing to increase the initial titer of the live attenuated viral antigen above a reliably safe level. As an additional benefit, the present invention provides a means for lowering the cost of manufacture of the vaccines provided by significantly reducing the amount of live attenuated viruses necessary to make such a safe and efficacious vaccine. In addition, the live attenuated virus vaccines of the present invention are more convenient to use than their lyophilized counterparts. Accordingly, the present invention provides safe and efficacious live attenuated virus vaccines that can be stored as liquids at refrigerated temperatures and still remain stable for 12 to 18 months or even longer.

Moreover surprisingly, the liquid stable live virus vaccines of the present invention can include canine and/or feline viruses of any type. Thus, the liquid stable live virus vaccines of the present invention can include both enveloped and non-enveloped viruses. In addition, the liquid stable live virus vaccines of the present invention can include live attenuated viruses having single-stranded RNA genomes, single-stranded DNA genomes, or double-stranded DNA genomes.

The use of singular terms for convenience in the description is in no way intended to be so limiting. Thus, for example, reference to a "sugar additive" includes reference to one or more of such sugar additives, unless otherwise specified. The use of plural terms is also not intended to be limiting, unless otherwise specified. Similarly, a chemical compound that can be referred to as an acid or its corresponding base, unless otherwise specified, when denoted herein as either is intended to mean either form of the compound. Thus, the use of the term glutamic acid is meant to include glutamate and vice versa.

As used herein, a "vaccine" is a composition that is suitable for application to an animal (including, in certain embodiments, humans) which upon administration to the animal induces an immune response strong enough to minimally aid in the protection from a clinical disease arising from an infection with a wild-type micro-organism, i.e., strong enough for aiding in the prevention of the clinical disease, and/or preventing, ameliorating, or curing the clinical disease. Unless expressly indicated otherwise, the use of the term vaccine includes multivalent vaccines.

As used herein, a "multivalent vaccine" is a vaccine that comprises two or more different antigens. In a particular embodiment of this type, the multivalent vaccine stimulates the immune system of the recipient against two or more different pathogens.

As used herein, a "liquid stable" vaccine is a vaccine maintained as a liquid (including a liquid multivalent vaccine) that remains efficacious for at least one year when stored at or below 7° C. (e.g., in a standard refrigerator, and/or at 0° C.-7° C.). In particular embodiments a liquid stable vaccine remains efficacious when stored at or below 7° C. for at least 1.5 years. In more particular embodiments a liquid stable vaccine remains efficacious when stored at or below 7° C. for at least 2 years. In still more particular embodiments a liquid stable vaccine remains efficacious when stored at or below 7° C. for at least 2.5 to 3 years.

As used herein, the terms "protect", "protecting", "provide protection to", "providing protection to", and "aids in the protection" do not require complete protection from any indication of infection. For example, "aids in the protection" can mean that the protection is sufficient such that, after challenge, symptoms of the underlying infection are at least reduced, and/or that one or more of the underlying cellular, physiological, or biochemical causes or mechanisms causing the symptoms are reduced and/or eliminated. It is understood that "reduced," as used in this context, means relative to the state of the infection, including the molecular state of the infection, not just the physiological state of the infection.

As used herein, the term "therapeutically effective amount" is an amount of a given antigen, e.g., live attenuated virus, which is sufficient to provide protection to and/or aid in the protection from the pathogen that the antigen is being administered to protect against, when provided in a single administration and/or when intended, provided as an initial administration with one or more subsequent booster administration(s).

As used herein, an "efficacious" vaccine comprises a therapeutically effective amount of a given antigen.

As used herein, the term "pharmaceutically acceptable" is used adjectivally to mean that the modified noun is appropriate for use in a pharmaceutical product. When it is used, for example, to describe an excipient in a pharmaceutical vaccine, it characterizes the excipient as being compatible with the other ingredients of the composition and not disadvantageously deleterious to the intended recipient.

The term "carrier" refers to a diluent, adjuvant, excipient, or vehicle with which the compound is administered. Pharmaceutical acceptable carriers can be sterile liquids, such as water and/or oils, including those of petroleum, animal, vegetable or synthetic origin, such as peanut oil, soybean oil, mineral oil, sesame oil and the like. Water or aqueous solution saline solutions and aqueous dextrose and glycerol solutions can be employed as carriers, particularly for injectable solutions.

As used herein, an "adjuvant" is a substance that is able to favor or amplify the cascade of immunological events, ultimately leading to a better immunological response, i.e., the integrated bodily response to an antigen. An adjuvant is in general not required for the immunological response to occur, but favors or amplifies this response.

As used herein, "systemic administration" is administration into the circulatory system of the body (comprising the cardiovascular and lymphatic system), thus affecting the body as a whole rather than a specific locus such as the gastro-intestinal tract (via e.g., oral or rectal administration) and the respiratory system (via e.g., intranasal administration). Systemic administration can be performed e.g., by administering into muscle tissue (intramuscular), into the dermis (intradermal, transdermal, or supradermal), underneath the skin (subcutaneous), underneath the mucosa (submucosal), in the veins (intravenous) etc.

"Parenteral administration" includes subcutaneous injections, submucosal injections, intravenous injections, intramuscular injections, intradermal injections, and infusion.

As used herein, the term "canine" includes all domestic dogs, *Canis lupus familiaris* or *Canis familiaris*, unless otherwise indicated.

Canine parvovirus "CPV" was first isolated in 1978 and was named CPV-2 to distinguish it from canine parvovirus Minute virus (CMV or CPV-1). Approximately a year after the initial isolation of CPV-2, a genetic variant, CPV-2a, was identified. In the mid-1980's, a second genetic variant, CPV-2b, was identified. CPV-2a and CPV-2b soon completely displaced CPV-2. Today, CPV-2a is no longer detected in the United States [Parrish and Kawaoka, *Annu Rev. Microbiol.*, 59:553-586 (2005)]. A fourth CPV variant in this family, CPV-2c, was first described in 2000 [see, U.S. Pat. No. 8,227, 593; U.S. Pat. No. 8,258,274; Hong et al., *J. Vet. Diagn. Invest.* (5):535-9 (2007)]. U.S. provisional application 61/739,067 filed Dec. 19, 2013, the contents of which are hereby incorporated by reference in their entireties, describes a specific attenuated CPV-2c isolate (ATCC accession No. PTA-13492) that was subsequently deposited on Jan. 24, 2013 with the American Type Culture Collection (ATCC) 10801 University Boulevard, Manassas, Va. 20110-2209, U.S.A., under conditions that satisfy the requirements of the Budapest Treaty on the International Recognition of the Deposit of Microorganisms for the Purposes of Patent Procedure. In addition, a recombinant canine parvovirus has been constructed that comprises a heterogenous CPV-2c/CPV-2 genome, i.e., the region encoding the capsid proteins is from a CPV-2c isolate and the region encoding the nonstructural proteins is from a CPV-2 isolate [WO2011107534 (A1); US 20120328652; WO2012007589 (A1) the contents of which are hereby incorporated by reference in their entireties]. As used herein, a vaccine of the present invention that comprises "canine parvovirus" can comprise one or more of these CPV types/variants/isolates, including the recently constructed recombinant canine parvovirus that comprises the heterogenous CPV-2c/CPV-2 genome.

As used herein, the term "feline" refers to any member of the Felidae family. Members of this family include wild, zoo, and domestic members, such as any member of the subfamilies Felinae, e.g., cats, lions, tigers, pumas, jaguars, leopards, snow leopards, panthers, North American mountain lions, cheetahs, lynx, bobcats, caracals or any cross breeds thereof. Cats also include domestic cats, pure-bred and/or mongrel companion cats, show cats, laboratory cats, cloned cats, and wild or feral cats.

As used herein a "sugar additive" is a 5 to 12 carbon sugar (e.g., sucrose, maltose, trehalose, dextrose, lactose, glucose, fructose, galactose) or sugar alcohol/polyol (e.g., sorbitol, mannitol, arabitol, inositol, maltitol). Unless otherwise specifically stated to the contrary, the percent (%) of the sugar additive is provided as a weight (w) of the sugar additive to the volume (v) of the vaccine, (w/v) in the vaccine.

As used herein, unless otherwise specifically stated to the contrary, the percent (%) of a solid additive, e.g., sugar additive or gelatin, in a vaccine is based on a 1% solution being 1 g of solid/100 ml of vaccine volume (w/v).

As used herein, unless otherwise specifically stated to the contrary, the percent (%) of a liquid additive, e.g., ethanol, in a vaccine is based on a 1% solution being 1 ml of liquid additive/100 ml of vaccine volume (v/v).

As used herein, unless otherwise specifically stated to the contrary, the pH value provided is the pH value determined/measured at 25° C.

The hydrolysate of whole casein that can be used in the liquid stable vaccines of the present invention can be obtained by a number of procedures including e.g., as an acid hydrolysate or an enzymatic hydrolysate. Such hydrolysates contain in the form of mixed amino acids and peptides all amino acids originally present in casein. One pancreatic hydrolysate of whole casein that can be used in the liquid stable vaccines of the present invention is sold as CASEIN HYDROLYSATE ENZYMATIC® by MP Biomedicals. Comparable products are sold under the name of NZ-AMINE®, NZ-AMINE® A, NZ-AMINE® AS, and NZ-AMINE® B, and Tryptone by Sigma-Aldrich.

Because the liquid stable vaccines of the present invention ideally range in pH from pH 6.0 to pH 8.0, the liquid stable vaccines of the present invention can comprise a buffer. Buffers for use in the liquid stable vaccines of the present invention include but are not limited to: Tris, Tris-Histidine, BIS-Tris, BIS-Tris-Propane, potassium and/or sodium phosphosphate, sodium or potassium pyrophosphate, imidazole, PIPES, ACES, MOPS, MOPSO, BES, TES, tricine, glycylglycine, and HEPES. The buffers can be brought to the desired pH with the use of any suitable counterion.

Multivalent Vaccines:

The present invention provides liquid stable multivalent vaccines. A liquid stable multivalent canine vaccine of the present invention for example, can include two or more of the following: canine distemper virus, canine adenovirus type 2, canine parvovirus, canine parainfluenza virus, canine influenza virus, canine pneumovirus, canine coronavirus, canine herpes virus, infectious canine hepatitis virus, canine minute virus, rabies virus, and pseudorabies virus. Such liquid stable vaccines can be subsequently combined with one or more attenuated or killed antigens such as *Bordetella bronchiseptica*, a *Mycoplasma* species, *Ehrlichia canis*, an *Anaplasma* species, *Leptospira canicola, Leptospira grippotyphosa, Leptospira hardjo, Leptospira icterohaemorrhagiae, Leptospira pomona, Leptospira interrogans, Leptospira autmnalis*, and *Leptospira Bratislava* prior to administration.

In addition, a liquid stable multivalent feline vaccine of the present invention can comprise one or more of the following feline pathogens: a feline herpesvirus, feline calicivirus, feline pneumovirus, feline parvovirus, feline leukemia virus, feline infectious peritonitis virus, feline immunodeficiency virus, borna disease virus, feline influenza virus, and avian influenza. Such liquid stable vaccines can be subsequently combined with attenuated or killed *Chlamydophila felis* and/or *Bartonella* spp. (e.g., *B. henselae*) prior to administration.

Vaccine Administration:

The liquid stable virus vaccines of the present invention may be administered by any conventional means, for example, by systemic administration, including by parenteral administration such as, without limitation, subcutaneous or intramuscular administration. The liquid stable virus vaccines of the present invention also may be administered by mucosal administration, such as by intranasal, oral, intratracheal, rectal, and/or ocular administration. Alternatively, the vaccines may be administered via a skin patch, scarification, or topical administration. It is contemplated that a liquid stable virus vaccine of the present invention also may be administered via the drinking water and/or food of the recipient felines and/or canines. It is further contemplated that such vaccines may be administered in the form of a treat or toy.

The vaccines (including multivalent vaccines) of the present invention also may be administered as part of a combination therapy, i.e., a therapy that includes, in addition to the vaccine itself, administering one or more additional active agents, therapies, etc. In that instance, it should be recognized that the amount of vaccine that constitutes a "therapeutically effective" amount may be more or less than the amount of vaccine that would constitute a "therapeutically effective" amount if the vaccine were to be administered alone. Other therapies may include those known in the art, such as, e.g., analgesics, fever-reducing medications, expectorants, anti-inflammation medications, antihistamines, and/or administration of fluids.

The immunogenicity level may be determined experimentally by challenge dose titration study techniques generally known in the art. Such techniques typically include vaccinating a number of animal subjects with the vaccine at different dosages and then challenging the animal subjects with the virulent virus to determine the minimum protective dose.

Factors affecting the preferred dosage regimen may include, for example, the species or breed (e.g., of a canine or feline), age, weight, sex, diet, activity, lung size, and condition of the subject; the route of administration; the efficacy, safety, and duration-of-immunity profiles of the particular vaccine used; whether a delivery system is used; and whether the vaccine is administered as part of a drug and/or vaccine combination. Thus, the dosage actually employed can vary for specific animals, and, therefore, can deviate from the typical dosages set forth above. Determining such dosage adjustments is generally within the skill of those in the art of vaccine development using conventional means.

Similarly, the volume with which such a dose can be administered typically lies between 0.1 mL (typical for intradermal or transdermal application) and 5.0 mL. A typical range for the administration volume is between 0.2 and 2.0 mL, and about 1.0 to 2.0 mL for intramuscular or subcutaneous administration.

It is contemplated that the vaccine may be administered to the vaccine recipient at a single time or alternatively, two or more times over days, weeks, months, or years. In some embodiments, the vaccine is administered at least two times. In certain such embodiments, for example, the vaccine is administered twice, with the second dose (e.g., a booster) being administered at least 2 weeks after the first dose. In particular embodiments, the vaccine is administered twice, with the second dose being administered no longer than 8 weeks after the first dose. In other embodiments, the second dose is administered from 1 week to 2 years after the first dose, from 1.5 weeks to 8 weeks after the first dose, or from 2 to 4 weeks after the first dose. In other embodiments, the second dose is administered about 3 weeks after the first dose.

In the above embodiments, the first and subsequent dosages may vary, such as in amount and/or form. Often, however, the dosages are the same in amount and form. When only a single dose is administered, the amount of vaccine in that dose alone generally comprises a therapeutically effective amount of the vaccine. When, however, more than one dose is administered, the amounts of vaccine in those doses together may constitute a therapeutically effective amount. In addition, a vaccine may be initially administered, and then a booster may be administered from 2 to 12 weeks later, as discussed above. However, subsequent administrations of the vaccine may be made on an annual (1-year) or bi-annual (2-year) basis, regardless as to whether a booster was administered or not.

The present invention may be better understood by reference to the following non-limiting Examples, which are provided as exemplary of the invention. The following Examples are presented in order to more fully illustrate embodiments of the invention. They should in no way be construed, however, as limiting the broad scope of the invention.

EXAMPLE

Example 1

Stability of Liquid Canine Virus Vaccines

Materials and Methods

Materials:

Cell culture grade sucrose and sorbitol are purchased from Fisher Scientific. Molecular grade L-Arginine hydrochloride, L-Methionine, L-Histidine, and sodium chloride with a purity of more than 98% are purchased from Sigma. Dextran sulfate with an average molecular weight 10,000 at a purity>95% is purchased from Sigma. Molecular biology grade ethanol (>99%), TWEEN 80, TWEEN 20, 1.0M Tris (pH 8.0) and EDTA (pH 8.0) solutions are purchased from Sigma. 20% Gelatin bloom 250 solution and 7.61% NZ Amine AS solution were prepared from the best available commercial reagents.

Bulking Antigen Preparation:

The following solutions have been prepared and sterilized by 0.2 µm filtration: 80% sucrose, 70% sorbitol, 1.0M L-Arginine (pH 7.2), 5% L-Methioinine, 5 mM dextran sulfate. Bulk antigens CDV, CAV2, CPV, and CPI having titers between 6.5 to 9.5 were frozen at −80° C. to be thawed immediately before blending.

Liquid Vaccine Blending and Filling:

The procedure to make a liquid vaccine CDV, CAV2, CPV, and CPI blend (1.0 mL per dose) is as follows: one dose amount of antigens are blended into different formulations as shown in Table 1 below, with target titers of 5.0 to 7.5 ($Log_{10}$ $TCID_{50}$) for the viral antigens. Prepare and label a 200 mL sterilized container, and then add each stabilizer and excipient component to the container following the calculated amount based on the final concentration of each component as shown in Table 1 below. Adjust with doubly distilled water (ddH2O) to the target volume for stabilizers and excipients. Mix on stirring plate for at least 10 min until all components are fully dissolved. Cool down and keep the stabilizer solution at 4° C. until the antigens are ready.

Thaw the frozen antigen in a 37° C. water bath with occasional shaking until almost all ice is melted. Some of the antigens have visible cell debris in the solution, so mix the antigens thoroughly before pipetting. The thawed antigen should be kept at 2-8° C. for no more than 8 hours prior to usage. Add an appropriate amount of CDV, CAV2, CPV, and CPI to the labeled container with the stabilizer solutions. Mix on the stirring plate until the antigens and stabilizers are homogeneously blended. Try to avoid generating bubbles and foams during this mixing step. Measure the pH at 25° C. and adjust the pH with either 1M HCL or 1M NaOH to the target pH if the pH is not within 7.2±0.1. Keep the vaccine blend at 2-8° C. until dispensing in the same day or aliquot into small volume and frozen at <−70° C. for future use. Dispense vaccine blend into 2 mL glass ampule vials at 1 mL per vial. Add argon gas to the ampule vials after filling to help prevent oxidation during storage, and then heat seal the ampule. Label the ampule with sample name, lot number, storage temperature, date and then transfer into boxes, and store at different temperature as designated.

Stability Testing at Accelerated Temperature and Real-Time:

Liquid samples were stored at 25° C.±1° C. and 4° C.±1° C., respectively in the corresponding incubators. 25° C. was used for accelerated stability testing for screening purposes, while the samples stored at 4° C. were the real-time stability samples. At the designated time point, 3 vials from each formulation was retrieved and the titer of each antigen was measured by cell culture based titration assay and reported as a median tissue culture infective dose ($TCID_{50}$) and/or as a 50% fluorescent antibody infective dose ($FAID_{50}$).

Analytical Methods

CPI Potency:

Dilutions of virus samples are inoculated onto dog kidney (DK) cells. After 4-6 days, monolayers are fixed and stained with fluorescein-conjugated CPI antiserum, and the virus titer is calculated by the Spearman-Karber Method [Cunningham, C. H. *A Laboratory Guide in Virology*, 7$^{th}$ edition, Burgess Publishing Co., Minneapolis, Minn. (1973); Kaplan, M. M. and Koprowski, H., Laboratory Techniques in Rabies, *World Health Organization, Switzerland*, (1973)]

CDV Potency:

Dilutions of virus samples were inoculated onto Vero cells. After 5-7 days, monolayers are observed for cytopathic effect, and the virus titer is calculated by the Spearman-Karber Method, as cited above.

CAV2 Potency:

Dilutions of virus samples were inoculated onto DK cells. After 7 days, monolayers are observed for cytopathic effect, and the virus titer is calculated by the Spearman-Karber Method, as cited above.

CPV Potency:

Dilutions of virus samples were inoculated onto DK cells. After 3 days, monolayers are stained with fluorescein-conjugated CPV antiserum, and the virus titer is calculated by the Spearman-Karber Method, as cited above.

Results

Accelerated Stability Testing at 25° C.:

Two studies have been carried out for liquid formulation screening. The first study includes formulations L-001 to L-008 and the second study includes formulations L-009 to L-026. (See Table 1 for details of the formulations.) Liquid samples stored in sealed glass ampule vials with 1 mL per vial per dose are tested at different time points after storage at 25° C. or 4° C. For 25° C. storage samples, the stability data for CDV, CAV2 and CPI are shown in Table 2. CPV was not tested for 25° C. storage since the liquid CPV is considered as the most stable fraction among the four viruses. For Study 1 samples that were incubated at 25° C. (L-001 to L-008) day 0, week 6, and week 8 data are used to compare the different formulations. For Study 2 samples that were incubated at 25° C. (L-009 to L-026) day 0, week 6, and week 12 samples are used for formulation screening. Additional time points in between have been tested and the trend is similar. Based on the degradation trend, the relative stability of each formulation are manually ranked as shown in Table 2 with five "+" being most stable and one "+" being the least stable. Each virus fraction is ranked individually and then the overall ranking accommodates all 3 viruses. Based on the ranking and comparison, a number of trends were observed. Accordingly, among the three saccharides tested (sucrose, sorbitol and glycerol), the stabilizing contribution of sucrose and sorbitol were significantly better than glycerol. There is also a strong preference for the higher concentration of sugar with 17%-25% combined sugar performing better than formulations with less than 10%. Among stabilizers from proteins or amino acids, 0.3M L-Arginine had the highest stability contribution, followed by 1% Methionine, 0.8% Gelatin and 1% NZ Amine. Among the other stabilizers, dextran sulfate and the free radical scavengers (FRS) appeared to contribute to the stability of the liquid CPV, CDV, CAV2 and CPI formulations, and although their presence does not significantly change the stability profile, they also had no negative effects on the stability. Therefore, in certain cases, it would be preferred that dextran sulfate and/or the FRS be included in the final formulation for the long-term storage stability of a liquid live feline or canine virus vaccine at 25° C. On the other hand, TWEEN 80 and TWEEN 20 were found to be detrimental to the stability of the virus formulations.

Real Time Stability Testing at 4° C.:

Long-term storage stability of liquid live CPV, CDV, CAV2 and CPI vaccines at 4° C. was also monitored and the data is presented in Table 3. The projected virus titer at 24 months at 4° C. is extrapolated from the data points at month 12 and month 18 for L-001 to L-008, and month 6 and 12 for L-009 to L-026 (see, Table 3 below). The minimum dose titer requirement for each virus at the expiration is listed at the bottom of Table 3 below, and is used to determine which formulation can provide a stable product at 4° C. There are ten formulations (L-009, L-011, L-012, L-014, L-15, L-016, L-018, L-019, L-025 and L-026) that were highly likely to produce a stable product, while formulations L-003 and L-007 have great potential to produce a stable product with a 2-years shelf life at 4° C. Among the four viruses examined, CDV appears to be the most labile. All ten formulations appear capable of providing greater than 3 years of stability at 0-8° C. for CAV2, CPV and CPI, and at least 2 years of stability at 0-8° C. for CDV.

TABLE 1

Liquid Live Canine Virus Vaccine Formulations

| Formulation Name | Formulation Details |
|---|---|
| L-001 | 25% Sorbitol, 10 mM Tris, 10 mM Histidine, pH 7.2 |
| L-002 | 15% Sorbitol, 10% Sucrose, 10 mM Tris, 10 mM Histidine, pH 7.2 |
| L-003 | 10% Sorbitol, 15% Sucrose, 10 mM Tris, 10 mM Histidine, pH 7.2 |
| L-004 | 15% Sorbitol, 10% Sucrose, 0.01% Tween 20, 10 mM Tris, 10 mM Histidine, pH 7.2 |
| L-005 | 75 mM NaCl, 5% Sucrose, 0.1 mM EDTA, 0.5% Ethanol, 0.02% Tween80, 10 mM Tris, 10 mM Histidine, pH 7.2 |
| L-006 | 75 mM NaCl, 5% Sucrose, 0.1 mM EDTA, 0.5% Ethanol, 0.02% Tween 80, 0.3M L-Arginine, 10 mM Tris, 10 mM Histidine, pH 7.2 |
| L-007 | 17% Sucrose, 0.8% Gelatin, 1.0% NZ Amine, 0.3M L-Arginine, 10 mM Tris, 10 mM Histidine, pH 7.2 |
| L-008 | 3.8% Sucrose, 0.8% Gelatin, 1.0% NZ Amine, 10 mM Tris, 10 mM Histidine, pH 7.2 |
| L-009 | 25% Sucrose, 1.6% Gelatin, 2.0% NZ Amine, 0.1 mM EDTA, 0.5% Ethanol, 10 mM Tris, 10 mM Histidine, pH 7.2 |
| L-010 | 25% Sucrose, 0.8% Gelatin, 1.0% NZ Amine, 0.01% Tween 80, 10 mM Tris, 10 mM Histidine, pH 7.2 |
| L-011 | 25% Sucrose, 0.3M Arginine, 50 uM Dextran Sulfate, 10 mM Tris, 10 mM Histidine, pH 7.2 |
| L-012 | 25% Sucrose, 1% Methionine,, 10 mM Tris, 10 mM Histidine, pH 7.2 |
| L-013 | 15% Sucrose, 10% Sorbitol, 1.6% Gelatin, 2.0% NZ Amine, 0.01% Tween 80, 10 mM Tris, 10 mM Histidine, pH 7.2 |
| L-014 | 15% Sucrose, 10% Sorbitol, 0.8% Gelatin, 1.0% NZ Amine, 0.1 mM EDTA, 0.5% Ethanol, 10 mM Tris, 10 mM Histidine, pH 7.2 |
| L-015 | 15% Sucrose, 10% Sorbitol, 0.3M Arginine,, 10 mM Tris, 10 mM Histidine, pH 7.2 |
| L-016 | 15% Sucrose, 10% Sorbitol, 1% Methionine, 50 uM Dextran Sulfate, 10 mM Tris, 10 mM Histidine, pH 7.2 |

TABLE 1-continued

Liquid Live Canine Virus Vaccine Formulations

| Formulation Name | Formulation Details |
|---|---|
| L-017 | 17% Sucrose, 0.3M L-Arginine, 1.6% Gelatin, 2.0% NZ Amine, 50 uM Dextran Sulfate, 10 mM Tris, 10 mM Histidine, pH 7.2 |
| L-018 | 17% Sucrose, 0.3M L-Arginine, 0.8% Gelatin, 1.0% NZ Amine, 10 mM Tris, 10 mM Histidine, pH 7.2 |
| L-019 | 17% Sucrose, 0.3M L-Arginine, 0.1 mM EDTA, 0.5% Ethanol, 10 mM Tris, 10 mM Histidine, pH 7.2 |
| L-020 | 17% Sucrose, 0.3M L-Arginine, 1% Methionine, 0.01% Tween 80, 10 mM Tris, 10 mM Histidine, pH 7.2 |
| L-021 | 40% Glycerol, 1.6% Gelatin, 2.0% NZ Amine,, 10 mM Tris, 10 mM Histidine, pH 7.2 |
| L-022 | 40% Glycerol, 0.8% Gelatin, 1.0% NZ Amine, 50 uM Dextran Sulfate, 10 mM Tris, 10 mM Histidine, pH 7.2 |
| L-023 | 40% Glycerol, 0.3M Arginine, 0.01% Tween 80, 10 mM Tris, 10 mM Histidine, pH 7.2 |
| L-024 | 40% Glycerol, 1% Methionine, 0.1 mM EDTA, 0.5% Ethanol, 10 mM Tris, 10 mM Histidine, pH 7.2 |

The unit of concentrations is: Sucrose (w/v), Sorbitol (w/v), Glycerol (v/v), Gelatin (w/v), NZ Amine (w/v), L-Arginine (M), Methionine (w/v), TWEEN (v/v), dextran sulfate (uM), ethanol (v/v), EDTA (mM), histidine (mM), Tris (mM), NaCl (M).

TABLE 2

Accelerated Stability Testing for Liquid Canine Virus Vaccine Formulations
Titer ($Log_{10}$ $TCID_{50}$) of each virus fraction during storage at 25° C. (weeks)

| | CDV | | | | CAV | | | | CPI | | | | 25° C. Overall |
|---|---|---|---|---|---|---|---|---|---|---|---|---|---|
| | 0 | 6 | 8 | Rank | 0 | 2 | 8 | Rank | 0 | 6 | 8 | Rank | |
| L-001 | 5.47 | 3.94 | 3.67 | +++++ | 5.33 | 5.95 | 6.50 | +++++ | 7.09 | 6.00 | 6.11 | ++++ | ++++ |
| L-002 | 5.47 | 3.56 | 3.83 | +++++ | 5.33 | 6.06 | 6.33 | +++++ | 7.09 | 6.67 | 6.61 | +++++ | ++++ |
| L-003 | 5.47 | 3.89 | 3.78 | +++++ | 5.33 | 5.83 | 6.39 | +++++ | 7.09 | 6.50 | 6.72 | +++++ | ++++ |
| L-004 | 5.47 | 3.06 | 3.40 | ++++ | 5.33 | 6.28 | 6.28 | +++++ | 7.09 | 6.33 | 6.06 | ++++ | ++++ |
| L-005 | 5.47 | 1.50 | | + | 5.33 | 6.17 | | + | 7.09 | 1.50 | | | + |
| L-006 | 5.47 | 1.56 | | + | 5.33 | 5.33 | | + | 7.09 | 1.72 | | | + |
| L-007 | 5.47 | 3.67 | 3.89 | +++++ | 5.33 | 5.78 | 5.94 | +++++ | 7.09 | 5.72 | 6.72 | +++++ | +++++ |
| L-008 | 5.47 | 1.56 | 1.50 | + | 5.33 | 6.78 | 7.11 | +++++ | 7.09 | 6.17 | 6.33 | ++++ | + |

| | 0 | 4 | 9 | Rank | 0 | 6 | 12 | Rank | 0 | 6 | 12 | Rank | |
|---|---|---|---|---|---|---|---|---|---|---|---|---|---|
| L-009 | 5.56 | 4.50 | 3.00 | ++ | 5.72 | 5.78 | 5.92 | +++++ | 7.44 | 5.83 | 5.84 | +++ | ++ |
| L-010 | 5.63 | 2.00 | 1.50 | + | 5.75 | 1.50 | 1.50 | + | 7.27 | 1.50 | 1.50 | + | + |
| L-011 | 5.83 | 5.11 | 3.92 | ++++ | 5.95 | 5.11 | 5.25 | ++++ | 7.17 | 6.67 | 7.17 | +++++ | ++++ |
| L-012 | 5.63 | 4.39 | 4.09 | ++++ | 5.75 | 5.33 | 5.75 | +++++ | 7.27 | 6.50 | 6.00 | +++ | ++++ |
| L-013 | 5.63 | 2.00 | 1.50 | + | 5.75 | 1.50 | 1.50 | + | 7.27 | 1.50 | 1.50 | + | + |
| L-014 | 5.63 | 4.72 | 3.34 | ++ | 5.75 | 5.39 | 5.92 | +++++ | 7.27 | 6.00 | 5.84 | +++ | ++ |
| L-015 | 5.61 | 4.72 | 4.25 | +++++ | 5.39 | 5.39 | 5.42 | +++++ | 7.34 | 6.61 | 6.75 | ++++ | +++++ |
| L-016 | 5.63 | 4.89 | 4.09 | ++++ | 5.75 | 5.72 | 5.67 | +++++ | 7.27 | 6.06 | 6.42 | ++++ | ++++ |
| L-017 | 5.63 | 4.83 | 3.59 | +++ | 5.75 | 5.61 | 5.67 | +++++ | 7.27 | 6.17 | 5.92 | +++ | +++ |
| L-018 | 5.72 | 4.78 | 4.00 | ++++ | 5.67 | 5.33 | 5.50 | +++++ | 7.61 | 6.11 | 6.75 | ++++ | ++++ |
| L-019 | 5.63 | 4.67 | 4.09 | ++++ | 5.75 | 5.00 | 5.67 | +++++ | 7.27 | 6.39 | 7.00 | +++++ | ++++ |
| L-020 | 5.22 | 1.78 | 1.50 | + | 5.78 | 1.50 | 1.50 | + | 7.39 | 1.50 | 1.50 | + | + |
| L-021 | 5.63 | 4.50 | 3.09 | ++ | 5.75 | 5.28 | 5.67 | +++++ | 7.27 | 5.33 | 4.83 | ++ | ++ |
| L-022 | 5.63 | 4.00 | 1.92 | + | 5.75 | 5.17 | 5.34 | ++++ | 7.27 | 5.44 | 5.17 | +++ | + |
| L-023 | 5.63 | 1.95 | 1.50 | + | 5.75 | 1.50 | 1.50 | + | 7.27 | 1.50 | 1.50 | + | + |
| L-024 | 5.67 | 4.17 | 1.83 | + | 5.94 | 5.17 | 5.75 | +++++ | 6.94 | 5.17 | 4.67 | ++ | + |
| L-025 | 5.78 | 4.72 | 3.92 | ++++ | 5.83 | 5.39 | 5.84 | +++++ | 7.00 | 6.39 | 7.00 | +++++ | ++++ |
| L-026 | 5.63 | 4.45 | 3.92 | ++++ | 5.75 | 5.28 | 5.59 | +++++ | 7.27 | 6.50 | 6.59 | ++++ | ++++ |

1) Study 1: Formulations L001-L008; Study 2: Formulations L-009 to L-026. These studies were performed at different time points.
2) CPV was not included in the 25° C. accelerated stability testing because it was shown to be relatively stable.
3) Ranking is based on the relative degradation curve extrapolated from these three time points, with five "+" being the best and one "+" being the worst. The overall ranking takes consideration of ranking for individual virus and is determined by the least stable fraction.

TABLE 3

Real Time Stability of Liquid Canine Virus Vaccine Formulations at 4° C.
Titer ($Log_{10}$ $TCID_{50}$) of each virus fraction during storage at 4° C. (months)

| | CDV | | | | CAV | | | | CPI | | | | CPV | | | | Overall Ranking |
|---|---|---|---|---|---|---|---|---|---|---|---|---|---|---|---|---|---|
| | 0 | 12 | 18 | 24* | 0 | 12 | 18 | 24* | 0 | 12 | 18 | 24* | 0 | 12 | 18 | 24* | |
| L-001 | 5.47 | 3.72 | 2.67 | 1.61 | 5.33 | 5.67 | 5.39 | 5.11 | 7.09 | 6.11 | 5.22 | 4.33 | 6.00 | 6.28 | 6.39 | 6.19 | + |
| L-002 | 5.47 | 3.56 | 3.00 | 2.44 | 5.33 | 5.67 | 5.66 | 5.66 | 7.09 | 6.67 | 5.83 | 5.00 | 6.00 | 6.55 | 6.51 | 6.46 | + |
| L-003 | 5.47 | 3.78 | 3.39 | 2.99 | 5.33 | 5.78 | 5.78 | 5.78 | 7.09 | 6.72 | 6.45 | 6.17 | 6.00 | 6.33 | 6.33 | 6.33 | +++ |
| L-004 | 5.47 | 2.83 | 3.00 | 2.80 | 5.33 | 5.83 | 5.89 | 5.69 | 7.09 | 6.67 | 5.99 | 5.31 | 6.00 | 6.39 | 6.39 | 6.39 | +++ |

TABLE 3-continued

Real Time Stability of Liquid Canine Virus Vaccine Formulations at 4° C.
Titer ($Log_{10}$ $TCID_{50}$) of each virus fraction during storage at 4° C. (months)

|  | CDV | | | | CAV | | | | CPI | | | | CPV | | | | Overall Ranking |
|---|---|---|---|---|---|---|---|---|---|---|---|---|---|---|---|---|---|
| L-007 | 5.47 | 3.83 | 3.17 | 2.50 | 5.33 | 5.78 | 5.83 | 5.63 | 7.09 | 6.78 | 6.83 | 6.63 | 6.00 | 5.11 | 4.78 | 4.45 | +++ |
| L-008 | 5.47 | 2.56 | 1.72 | 0.88 | 5.33 | 6.22 | 5.94 | 5.66 | 7.09 | 6.22 | 6.11 | 6.00 | 6.00 | 5.95 | 6.28 | 6.08 | + |
|  | 0 | 6 | 12 | 24* | 0 | 6 | 12 | 24* | 0 | 6 | 12 | 24* | 0 | 6 | 12 | 24* |  |
| L-009 | 5.56 | 3.72 | 4.06 | 3.86 | 5.72 | 6.28 | 6.22 | 6.16 | 7.44 | 6.50 | 6.22 | 5.94 | 6.00 | 4.72 | 4.89 | 4.69 | +++++ |
| L-011 | 5.83 | 4.33 | 4.39 | 4.19 | 5.95 | 5.61 | 5.83 | 5.63 | 7.17 | 7.28 | 7.16 | 7.05 | 6.00 | 6.06 | 5.61 | 5.17 | +++++ |
| L-012 | 5.63 | 4.33 | 4.50 | 4.30 | 5.75 | 6.22 | 5.78 | 5.34 | 7.27 | 7.28 | 6.89 | 6.50 | 6.00 | 6.50 | 6.67 | 6.47 | +++++ |
| L-014 | 5.63 | 3.94 | 3.94 | 3.94 | 5.75 | 6.17 | 6.00 | 5.83 | 7.27 | 7.00 | 6.67 | 6.34 | 6.00 | 6.06 | 5.94 | 5.83 | +++++ |
| L-015 | 5.61 | 4.06 | 4.39 | 4.19 | 5.39 | 6.11 | 5.89 | 5.67 | 7.34 | 7.33 | 7.33 | 7.13 | 6.00 | 6.22 | 6.05 | 5.88 | +++++ |
| L-016 | 5.63 | 3.95 | 4.00 | 3.80 | 5.75 | 5.89 | 5.83 | 5.77 | 7.27 | 7.00 | 6.94 | 6.88 | 6.00 | 6.61 | 5.83 | 5.05 | +++++ |
| L-017 | 5.63 | 4.22 | 4.06 | 3.89 | 5.75 | 6.22 | 6.17 | 6.11 | 7.27 | 7.39 | 7.00 | 6.62 | 6.00 | 5.06 | 4.56 | 4.06 | +++ |
| L-018 | 5.72 | 4.17 | 4.33 | 4.13 | 5.67 | 6.22 | 5.89 | 5.55 | 7.61 | 7.00 | 7.11 | 6.91 | 6.00 | 5.33 | 5.17 | 5.00 | +++++ |
| L-019 | 5.63 | 4.33 | 4.11 | 3.89 | 5.75 | 5.89 | 6.06 | 5.86 | 7.27 | 7.17 | 7.22 | 7.02 | 6.00 | 6.16 | 6.39 | 6.19 | +++++ |
| L-021 | 5.63 | 1.50 | 1.50 | 1.50 | 5.75 | 1.50 | 1.50 | 1.50 | 7.27 | n/d | n/d | n/d | 6.00 | n/d | n/d | n/d | + |
| L-022 | 5.63 | 1.50 | 1.50 | 1.50 | 5.75 | 1.50 | 1.50 | 1.50 | 7.27 | n/d | n/d | n/d | 6.00 | n/d | n/d | n/d | + |
| L-025 | 5.78 | 4.17 | 4.72 | 4.52 | 5.83 | 6.33 | 6.00 | 5.67 | 7.00 | 7.22 | 6.83 | 6.44 | 6.00 | 5.33 | 5.17 | 5.00 | +++++ |
| L-026 | 5.63 | 4.00 | 4.95 | 4.75 | 5.75 | 6.22 | 6.39 | 6.19 | 7.27 | 7.17 | 7.05 | 6.94 | 6.00 | 5.44 | 5.11 | 4.78 | +++++ |
| Minimum Expiration Titer |  |  | 3.70 |  |  |  | 4.80 |  |  |  | 5.10 |  |  |  | 4.30 |  |  |

1) n/d, not determined;
2) The minimum expiration titer is the product specification on the vaccine product at the end of 2 years shelf life at 4° C.
3) Denoted as 24* above, the titer for 24 months at 4° C. is extrapolated from the previous three time points i.e, the projected virus titer at 24 months at 4° C. is extrapolated from the data points at Time "0", month 12, and month 18 for L-001 to L-008; and Time "0", month 6, and 12 for L-009 to L-026.
4) Time "0" titer is from the blend immediately after mixing and preparation of vaccine mixture..

We claim:

1. A liquid stable vaccine that comprises a live attenuated canine or feline virus, 10-30% (w/v) sugar additive, and an amino acid; wherein the liquid stable vaccine has a pH of 6.0 to 8.0; wherein the amino acid is selected from the group consisting of arginine and methionine; wherein when the amino acid is arginine, its final concentration in the liquid stable vaccine is 0.15 to 0.6 M; and wherein when the amino acid is methionine, its final concentration in the liquid stable vaccine is 0.025 to 0.3 M; and
   wherein the live attenuated canine or feline virus is selected from the group consisting of a distemper virus, an adenovirus, a parvovirus, and a parainfluenza virus.

2. The liquid stable vaccine of claim 1, wherein the live attenuated canine virus is selected from the group consisting of canine distemper virus, canine adenovirus type 2, canine parvovirus, and canine parainfluenza virus.

3. The liquid stable vaccine of claim 2 wherein the canine parvovirus (CPV) is selected from the group consisting of CPV-2, CPV-2a, CPV-2b, CPV-2c, and a recombinant CPV comprising a heterogenous CPV-2c/CPV-2 genome.

4. The liquid stable vaccine of claim 1 that further comprises 0.4 to 1.6% (w/v) gelatin.

5. The liquid stable vaccine of claim 4 that further comprises 0.5-2.0% (w/v) of a proteolytic hydrolysate of whole casein.

6. The liquid stable vaccine of claim 1 that further comprises 0.25 to 1.0% (v/v) ethanol.

7. The liquid stable vaccine of claim 6 that further comprises 50 to 200 μM EDTA.

8. The liquid stable vaccine of claim 1 that further comprises a buffer.

9. The liquid stable vaccine of claim 8 wherein the buffer comprises 2.5 to 50 mM Tris.

10. The liquid stable vaccine of claim 9, wherein the buffer further comprises 2.5 to 50 mM histidine.

11. The liquid stable vaccine of claim 1, wherein the sugar additive is selected from the group consisting of sucrose, sorbitol, and a combination of sucrose and sorbitol.

12. The liquid stable vaccine of claim 1, wherein the live attenuated virus is canine distemper virus.

13. The liquid stable vaccine of claim 12 that further comprises a live attenuated canine parvovirus (CPV).

14. The liquid stable vaccine of claim 13 wherein the CPV is selected from the group consisting of CPV-2, CPV-2a, CPV-2b, CPV-2c, and a recombinant CPV comprising a heterogenous CPV-2c/CPV-2 genome.

15. The liquid stable vaccine of claim 14 that further comprises a live attenuated canine adenovirus type 2.

16. The liquid stable vaccine of claim 15 that further comprises a live attenuated canine parainfluenza virus.

17. A method of vaccinating a canine against canine distemper virus, canine adenovirus type 2, canine parvovirus, and canine parainfluenza virus comprising administering to the canine the liquid stable vaccine of claim 16.

18. A method of vaccinating a canine against a canine virus comprising administering to the canine the liquid stable vaccine of claim 1.

19. The method of claim 18, wherein said administering is performed by subcutaneous injection.

20. A method of making a liquid stable vaccine that comprises combining a therapeutically effective amount of a live attenuated canine or feline virus with a 10-30% (w/v) sugar additive, an amino acid, and a buffered solution at pH 6.0 to pH 8.0 to form a liquid stable vaccine;
   wherein the amino acid is selected from the group consisting of arginine and methionine; wherein when the amino acid is arginine, its final concentration in the liquid stable vaccine is 0.15 to 0.6 M; and wherein when the amino acid is methionine, its final concentration in the liquid stable vaccine is 0.025 to 0.3 M; and
   wherein the live attenuated canine or feline virus is selected from the group consisting of a distemper virus, an adenovirus, a parvovirus, and a parainfluenza virus.

21. The liquid stable vaccine of claim 1, wherein the live attenuated feline virus is a feline panleukopenia virus.

* * * * *